United States Patent
Eichhorn

(10) Patent No.: US 9,305,023 B2
(45) Date of Patent: Apr. 5, 2016

(54) STORING AND RETRIEVING LARGE IMAGES VIA DICOM

(71) Applicant: Leica Biosystems Imaging, Inc., Vista, CA (US)

(72) Inventor: Ole Eichhorn, Westlake Village, CA (US)

(73) Assignee: LEICA BIOSYSTEMS IMAGING, INC, Vista, CA (US)

( * ) Notice: Subject to any disclaimer, the term of this patent is extended or adjusted under 35 U.S.C. 154(b) by 0 days.

(21) Appl. No.: 14/305,216

(22) Filed: Jun. 16, 2014

(65) Prior Publication Data
US 2014/0294267 A1 Oct. 2, 2014

Related U.S. Application Data

(63) Continuation of application No. 13/337,882, filed on Dec. 27, 2011, now Pat. No. 8,781,261, which is a continuation of application No. 11/771,612, filed on Jun. 29, 2007, now Pat. No. 8,086,077.

(60) Provisional application No. 60/806,438, filed on Jun. 30, 2006.

(51) Int. Cl.
| G06K 9/60 | (2006.01) |
| G06F 12/00 | (2006.01) |
| G06F 17/30 | (2006.01) |
| G06F 19/00 | (2011.01) |

(52) U.S. Cl.
CPC ...... *G06F 17/30244* (2013.01); *G06F 17/3028* (2013.01); *G06F 19/321* (2013.01)

(58) Field of Classification Search
None
See application file for complete search history.

(56) References Cited

U.S. PATENT DOCUMENTS

| 3,643,015 A | 2/1972 | Egger |
| 4,673,988 A | 6/1987 | Jansson et al. |
| 4,700,298 A | 10/1987 | Palcic et al. |
| 4,742,558 A | 5/1988 | Ishibashi et al. |
| 4,744,642 A | 5/1988 | Yoshinaga et al. |
| 4,760,385 A | 7/1988 | Jansson et al. |
| 4,777,525 A | 10/1988 | Preston |
| 4,845,552 A | 7/1989 | Jaggi et al. |
| 4,960,999 A | 10/1990 | McKean et al. |

(Continued)

FOREIGN PATENT DOCUMENTS

| JP | 09-102928 | 4/1997 |
| JP | 2001-251596 A | 9/2001 |

(Continued)

OTHER PUBLICATIONS

DICOM Standards Committee "JPEG 2000 Transfer Syntaxes", Jan. 2002, in 27 pages.

(Continued)

*Primary Examiner* — Randolph I Chu
(74) *Attorney, Agent, or Firm* — Procopio, Cory, Hargreaves & Savitch LLP

(57) ABSTRACT

Systems, methods, and media for storing a digital image using the Digital Imaging and Communication in Medicine (DICOM) standard. In an embodiment, a digital image at a first resolution is divided into a plurality of regions. Each of the plurality of regions is stored as a separate DICOM image file. In addition, each of the DICOM image files is associated with a DICOM series representing the digital image at the first resolution.

17 Claims, 2 Drawing Sheets

(56) References Cited

U.S. PATENT DOCUMENTS

| | | | |
|---|---|---|---|
| 5,086,477 A | 2/1992 | Yu et al. | |
| 5,187,754 A | 2/1993 | Currin et al. | |
| 5,231,663 A | 7/1993 | Earl | |
| 5,400,145 A | 3/1995 | Suita et al. | |
| 5,412,214 A | 5/1995 | Suzuki et al. | |
| 5,495,535 A | 2/1996 | Smilansky et al. | |
| 5,578,832 A | 11/1996 | Trulson et al. | |
| 5,633,948 A | 5/1997 | Kegelmeyer et al. | |
| 5,644,356 A | 7/1997 | Swinson | |
| 5,672,861 A | 9/1997 | Fairley et al. | |
| 5,710,835 A | 1/1998 | Bradley | |
| 5,714,756 A | 2/1998 | Park et al. | |
| 5,790,710 A | 8/1998 | Price et al. | |
| 5,793,969 A | 8/1998 | Kamentsky et al. | |
| 5,796,861 A | 8/1998 | Vogt et al. | |
| 5,834,758 A | 11/1998 | Trulson et al. | |
| 5,872,591 A | 2/1999 | Truc et al. | |
| 5,912,699 A | 6/1999 | Hayenga et al. | |
| 5,922,282 A | 7/1999 | Ledley et al. | |
| 5,943,122 A | 8/1999 | Holmes | |
| 5,963,314 A | 10/1999 | Worster et al. | |
| 5,968,731 A | 10/1999 | Layne et al. | |
| 5,991,444 A | 11/1999 | Burt et al. | |
| 5,999,662 A | 12/1999 | Burt et al. | |
| 6,002,789 A | 12/1999 | Olsztyn et al. | |
| 6,005,964 A | 12/1999 | Reid et al. | |
| 6,049,421 A | 4/2000 | Raz et al. | |
| 6,078,681 A | 6/2000 | Silver et al. | |
| 6,091,846 A | 7/2000 | Lin et al. | |
| 6,101,265 A | 8/2000 | Bacus et al. | |
| 6,272,235 B1 | 8/2001 | Bacus et al. | |
| 6,327,377 B1 | 12/2001 | Rutenberg et al. | |
| 6,330,348 B1 | 12/2001 | Kerschmann et al. | |
| 6,438,268 B1 | 8/2002 | Cockshott et al. | |
| 6,519,357 B2 | 2/2003 | Takeuchi | |
| 6,711,283 B1 | 3/2004 | Soenksen | |
| 6,714,281 B1 | 3/2004 | Amano et al. | |
| 7,027,628 B1* | 4/2006 | Gagnon et al. | 382/128 |
| 7,467,160 B2 | 12/2008 | McIntyre | |
| 8,086,077 B2 | 12/2011 | Eichhorn | |
| 8,781,261 B2 | 7/2014 | Eichhorn | |
| 2002/0073429 A1 | 6/2002 | Beane et al. | |
| 2002/0102028 A1 | 8/2002 | Keller et al. | |
| 2002/0191867 A1* | 12/2002 | Le et al. | 382/300 |
| 2003/0005464 A1 | 1/2003 | Gropper et al. | |
| 2003/0221017 A1* | 11/2003 | Kim | 709/247 |
| 2003/0223650 A1* | 12/2003 | Kim | 382/302 |
| 2004/0032968 A1* | 2/2004 | Andrew et al. | 382/100 |
| 2004/0070678 A1 | 4/2004 | Toyama et al. | |
| 2004/0111415 A1 | 6/2004 | Scardino et al. | |
| 2004/0114810 A1* | 6/2004 | Boliek et al. | 382/232 |
| 2004/0146205 A1* | 7/2004 | Becker et al. | 382/232 |
| 2004/0175046 A1 | 9/2004 | Gormish | |
| 2004/0175059 A1 | 9/2004 | Willner et al. | |
| 2004/0205199 A1 | 10/2004 | Gormish | |
| 2004/0208380 A1 | 10/2004 | Aoki et al. | |
| 2005/0007625 A1 | 1/2005 | Garcia | |
| 2005/0273514 A1 | 12/2005 | Milkey et al. | |
| 2006/0083442 A1 | 4/2006 | Loukipoudis et al. | |
| 2006/0095540 A1 | 5/2006 | Anderson et al. | |
| 2006/0111083 A1 | 5/2006 | Goss | |
| 2006/0226232 A1 | 10/2006 | Helkio et al. | |
| 2007/0118536 A1 | 5/2007 | McIntyre et al. | |
| 2007/0230829 A1 | 10/2007 | Sirohey et al. | |
| 2007/0237402 A1 | 10/2007 | Dekel et al. | |
| 2009/0100096 A1 | 4/2009 | Erlichson et al. | |
| 2011/0153776 A1* | 6/2011 | Opala et al. | 709/217 |
| 2012/0200580 A1* | 8/2012 | Gnanasambandam et al. | 345/505 |
| 2013/0103647 A1* | 4/2013 | Ho et al. | 707/661 |

FOREIGN PATENT DOCUMENTS

| | | |
|---|---|---|
| JP | 2002-008008 A | 1/2002 |
| JP | 2004-106196 A | 4/2004 |
| JP | 2005-018734 A | 1/2005 |
| JP | 2005-176245 A | 6/2005 |
| JP | 2005-524072 A | 8/2005 |
| JP | 2005-283418 A | 10/2005 |
| JP | 2005-316990 A | 11/2005 |
| JP | 2006-146604 A | 6/2006 |
| JP | 2006-164211 A | 6/2006 |
| WO | 2004077338 A2 | 9/2004 |
| WO | 2008005868 A2 | 1/2008 |

OTHER PUBLICATIONS

Gormish et al. "JPEG 200: Overview. archtecture, and Applications", 2000, IEEE, in 4 pages.
European Search Report dated Aug. 19, 2009 from related European Application No. 07840329.2, in 4 pages.
Written Opinion issued in PCT/US2007/072527 on Jun. 17, 2008, in 5 pages.
International Search Report/Written Opinion issued in PCT/US2007/072540 on Sep. 23, 2008, in 10 pages.
European Search Report dated Oct. 13, 2011 for related European Application No. 07799195.8, in 6 pages.
Office Action dated Sep. 18, 2012 for related Japanese Patent Application No. 2009-518586 (now JP Patent No. 5484048), and corresponding English translation, in 4 pages.
Office Action dated Aug. 6, 2013 for related Japanese Patent Application No. 2009-518586 (now JP Patent No. 5484048), and corresponding English translation, in 5 pages.

* cited by examiner

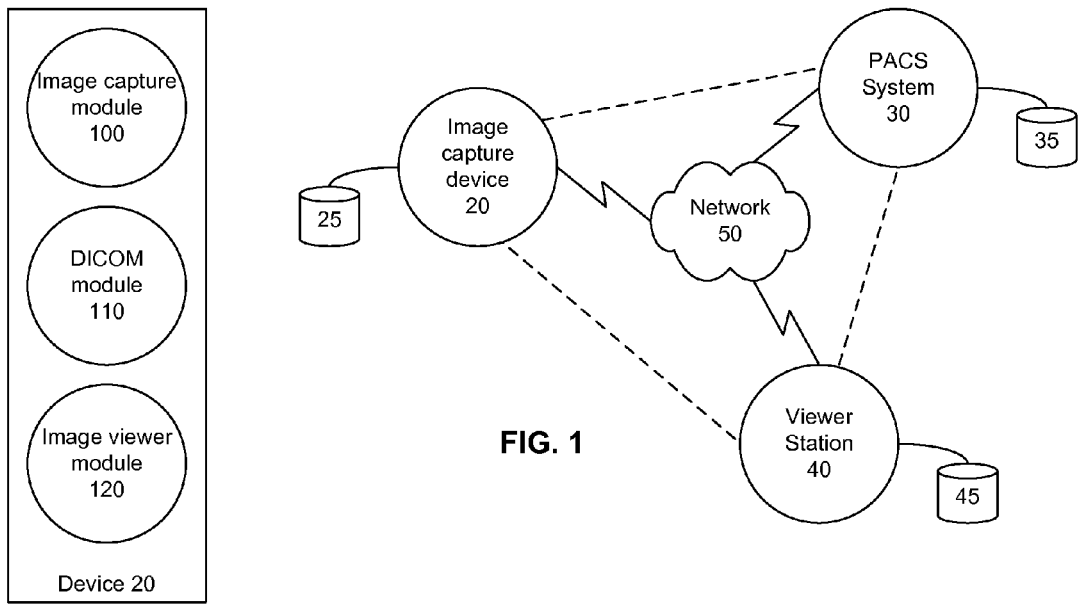
FIG. 1
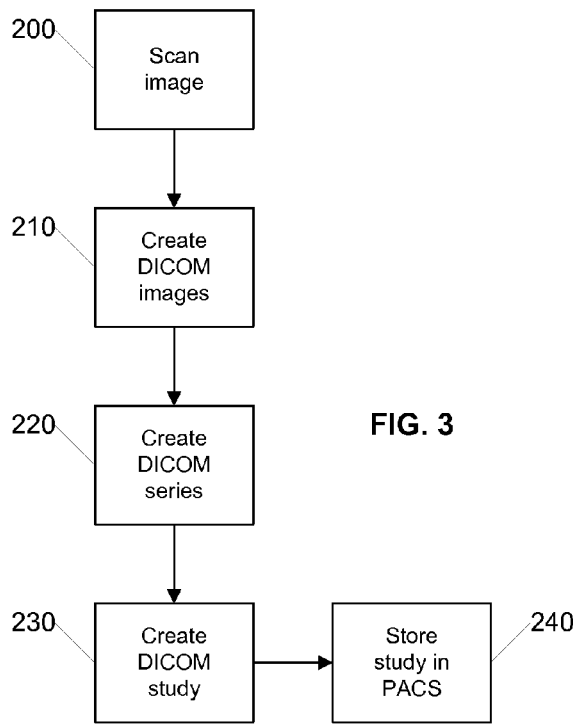
FIG. 2
FIG. 3
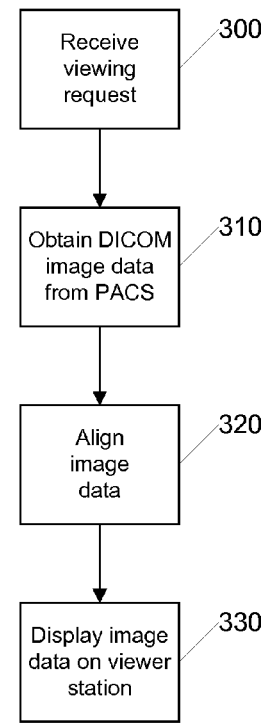
FIG. 4

STORING AND RETRIEVING LARGE IMAGES VIA DICOM

CROSS-REFERENCE TO RELATED APPLICATIONS

The present application is a continuation of U.S. patent application Ser. No. 13/337,882, filed on Dec. 27, 2011, which is a continuation of U.S. patent application Ser. No. 11/771,612, filed on Jun. 29, 2007 and issued as U.S. Pat. No. 8,086,077, which claims priority to U.S. Provisional Patent App. No. 60/806,438, filed on Jun. 30, 2006, all of which are hereby incorporated herein by reference in their entireties.

BACKGROUND

1. Field of the Invention

The present invention is generally related to digital pathology.

2. Related Art

The Digital Imaging and Communication in Medicine ("DICOM") standard is maintained by the National Electronic Manufacturer's Association ("NEMA"), and is supported by large image management systems called Picture Archive and Communication Systems ("PACS"). PACS systems are used in hospitals and labs to store, archive, retrieve, search, and manage images used for clinical and research purposes in medicine, most typically for Radiology images such as radiography (e.g., X-Rays), computed tomography ("CT") scans, positron emission tomography ("PET"), and magnetic resonance imaging ("MRI"), but also for other modalities such as Ultrasonography, Cardiology, Endoscopy, and Mammography. A large number of clinical and laboratory instruments support DICOM-standard messaging as a means to communicate image information and store it in PACS systems.

The field of pathology is undergoing a transformation in which digital imaging is becoming increasingly important. This transformation is fueled by the commercial availability of instruments for digitizing microscope slides, such as the Aperio ScanScope® described in U.S. Pat. No. 6,711,283 which is incorporated herein by reference in its entirety. The whole-slide images ("WSI" or "digital slides") made by digitizing microscope slides at diagnostic resolution are very large. Frequently multiple images are created at varying resolutions to facilitate rapid panning and zooming for pathologists. The set of images comprising a single scanned digital slide are typically stored as a single Tagged Image File Format ("TIFF") file. (TIFF is an open-source standard.) In addition to the size of digital slides, the access characteristics of these images differ from other images presently stored in PACS systems. Pathologists need the ability to rapidly pan and zoom when viewing images.

Unfortunately, there are several limitations of the DICOM standard which impact storage of digital slides. These limitations include DICOM's use of signed 16-bit integers to store the pixel dimensions of images, therefore the maximum image dimensions which can be stored are 32K×32K pixels. This is considerably smaller than a typical digital slide image, and two orders of magnitude smaller than an extremely large digital slide image. Additionally, DICOM uses signed 32-bit integers to store the object size of images, therefore the maximum compressed size of an image is 2 GB. In actual practice many PACS systems are not capable of handling individual images this large; because these PACS systems frequently decompress image data in memory, thereby limiting the maximum uncompressed size of images to 2 GB, they restrict the limit on compressed image size to something considerably smaller. Additionally, while DICOM provides the capability of accessing individual images in a series, as well as individual images in an entire series or entire study, it does not provide the capability of accessing subregions of an individual image. As noted above, the capability to access subregions is important to provide rapid panning and zooming.

Furthermore, the DICOM standard does not make provision for large two-dimensional images such as the digital slides being created for pathology, nor does it incorporate a way to handle images that are logically divided into subregions, nor does it incorporate a way to handle multiple images at varying resolutions. The process for evolving the DICOM standard is well-defined but slow moving, and even after the standard is enhanced to support digital slides it will be years before PACS and instrument vendors implement the enhanced standard. In the meantime, a means of using the currently implemented DICOM standard for storing digital slides is needed. Therefore, what is needed is a system and method that facilitates use of the currently implemented DICOM standard for storing and viewing digital slides.

SUMMARY

Accordingly, to provide a solution for storing and retrieving large images via DICOM and to facilitate integration of digital pathology into hospitals and laboratories, described herein are systems and methods that acquire digital slides and store these images into commercially available PACS systems using DICOM-standard messaging. Once a digital slide is stored in the PACS system, the PACS capabilities for storing, archiving, retrieving, searching, and managing images are leveraged for these new types of images. Additionally, because any particular case, or experiment may comprise images from multiple modalities, including radiology and pathology, all the images for a case or experiment could be managed together in a PACS system. Other features and advantages of the present invention will become more readily apparent to those of ordinary skill in the art after reviewing the following detailed description and accompanying drawings.

In an embodiment, a non-transitory computer-readable medium has instructions stored thereon that, when executed by a processor, cause the processor to, for each of one or more digital images: divide the digital image at a first resolution into a first plurality of regions; store each of the first plurality of regions as a separate first DICOM image file; associate each of the first DICOM image files with a first DICOM series representing the digital image at the first resolution; obtain the digital image at a second resolution that is different than the first resolution; divide the digital image at the second resolution into a second plurality of regions; store each of the second plurality of regions as a separate second DICOM image file; associate each of the second DICOM image files with a second DICOM series representing the digital image at the second resolution; and associate the first DICOM series and the second DICOM series with a DICOM study representing the digital image at a plurality of resolutions.

In an embodiment, a system for storing a digital image using the DICOM standard comprises: at least one hardware processor; and one or more modules that, when executed by the at least one hardware processor, for each of one or more digital images, divide the digital image at a first resolution into a first plurality of regions, store each of the first plurality of regions as a separate first DICOM image file, associate each of the first DICOM image files with a first DICOM series representing the digital image at the first resolution, obtain the digital image at a second resolution that is different than the first resolution, divide the digital image at the second resolution into a second plurality of regions, store each of the second plurality of regions as a separate second DICOM image file, associate each of the second DICOM image files with a second DICOM series representing the digital image at the second resolution, and associate the first DICOM series and the second DICOM series with a DICOM study representing the digital image at a plurality of resolutions.

In an embodiment, a method for storing a digital image using the DICOM standard comprises using at least one hardware processor to, for each of one or more digital images: divide the digital image at a first resolution into a first plurality of regions; store each of the first plurality of regions as a separate first DICOM image file; associate each of the first DICOM image files with a first DICOM series representing the digital image at the first resolution; obtain the digital image at a second resolution that is different than the first resolution; divide the digital image at the second resolution into a second plurality of regions; store each of the second plurality of regions as a separate second DICOM image file; associate each of the second DICOM image files with a second DICOM series representing the digital image at the second resolution; and associate the first DICOM series and the second DICOM series with a DICOM study representing the digital image at a plurality of resolutions.

BRIEF DESCRIPTION OF THE DRAWINGS

The details of the present invention, both as to its structure and operation, may be gleaned in part by study of the accompanying drawings, in which like reference numerals refer to like parts, and in which:

FIG. 1 is a network diagram illustrating an example system for storing and retrieving large images via DICOM according to an embodiment of the present invention;

FIG. 2 is a block diagram illustrating an example image capture device according to an embodiment of the present invention;

FIG. 3 is a flow diagram illustrating an example process for image capture and storage according to an embodiment of the present invention;

FIG. 4 is a flow diagram illustrating an example process for image retrieval and viewing according to an embodiment of the present invention;

DETAILED DESCRIPTION

Figure 5:
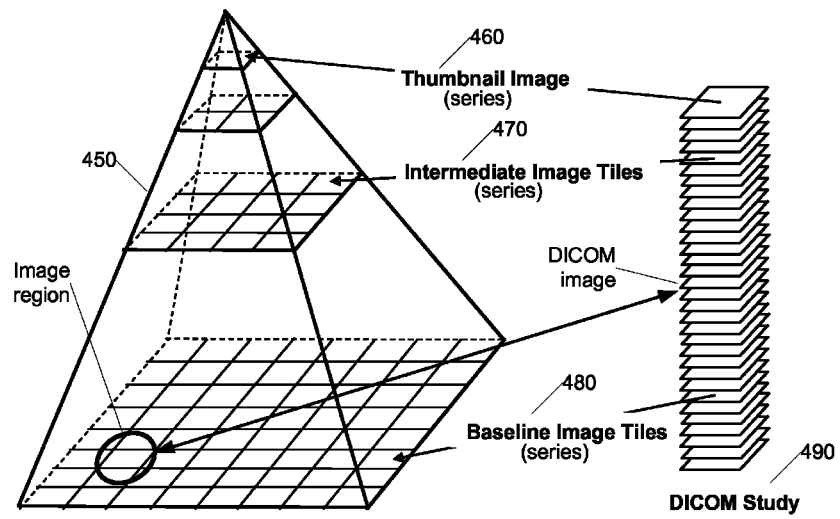
FIG. 5 is a block diagram illustrating a data mapping from a digital slide to a DICOM study according to an embodiment of the present invention.

Certain embodiments as disclosed herein provide for storing and retrieving large images via DICOM. After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention as set forth in the appended claims.

FIG. 1 is a network diagram illustrating an example system for storing and retrieving large images via DICOM according to an embodiment of the present invention. In the illustrated embodiment, the system comprises an image capture device 20 configured with a data storage area 25, a PACS system 30 configured with a data storage area 35, and a viewer station 40 configured with a data storage area 45. Each of these devices in the illustrated embodiment may be connected to the other by way of network 50 or by way of a direct connection, represented by the dashed lines in the figure.

As will be understood by those skilled in the art, the various devices can be implemented as physically separate devices or they may be combined in alternative ways such that certain functions are performed at one device while other functions are performed at a second device or a third device. These implementation choices are contemplated by the broad scope of the invention and the following discussion of a particular embodiment is therefore presented by way of example only and is not to be construed as limiting the claims in any fashion.

The image capture device 20 can be any of a variety of digital slide image capture devices. The function of the image capture device is to scan a high resolution image of a microscope slide and also scan or otherwise create images of the same slide at lower resolutions. The digital slides may be stored in data storage area 25.

The PACS system 30 can be any of a variety of PACS systems. The function of the PACS system is to store imagery data using the DICOM standard. DICOM stores images as two-dimensional arrays of pixels. Multiple images may be part of a series, and multiple series may be part of a study. From there studies may be part of a case, and multiple cases may be stored for a given patient and laboratory. This organization has its root in Radiology imaging. Radiology modalities like CT-scans and MRI capture studies which comprise multiple series of images separated in space and/or time. The individual images are typically small and manageable, although in aggregate an entire study comprising tens of series and hundreds of images may be much larger.

The viewer station 40 is configured to allow a user to view images from the PACS system 30 or the image capture device 20. The viewer station 40 may be connected directly to the image capture device 20 and the PACS system 30 or it may be connected indirectly, for example through network 50. The viewer station is configured with a data storage area 45.

FIG. 2 is a block diagram illustrating an example image capture device 20 according to an embodiment of the present invention. In the illustrated embodiment, the device 20 comprises an image capture module 100, a DICOM module 110, and an image viewer module 120. These modules can be implemented in a single device as shown or in separate devices as desired.

The image capture module 100 is configured to manage the image capture process in order to scan a physical microscope slide and create a digital slide that may have one or more levels of resolution. The DICOM module 110 is configured to logically arrange a digital slide into many smaller individual regions, and store each individual region as a DICOM image. A plurality of DICOM images that are all at the same resolution are identified together by the DICOM module 110 as a DICOM series. If a digital slide is translated into multiple DICOM series (e.g., if it includes multiple images at varying resolutions), then the digital slide is stored as a DICOM study, and each set of DICOM images at a particular resolution are stored together as a separate DICOM series in the DICOM study. The following table shows this mapping:

| Pathology object | DICOM object |
| --- | --- |
| digital slide | DICOM study |
| Image at varying resolution | DICOM series |
| 2D subregion of image | DICOM image |

In one embodiment, a digital slide is captured under the control of the image capture module 100, for example by scanning a region of a microscope slide with dimensions 20 mm×10 mm, at a resolution of 0.25 microns/pixel. The resulting image will have dimensions 80,000×40,000 pixels. Another image with a resolution of 1 micron/pixel may be created from this with dimensions 20,000×10,000 pixels, and another image with a resolution of 4 microns/pixel may be created with dimensions 5,000×2,500 pixels, and finally a fourth image with a resolution of 16 microns/pixel may be created with dimensions 1,250×750 pixels.

The DICOM module 110 then takes each of these images (each is at a different resolution) and logically arranges each image into regions of dimension 500×500 pixels, which is a typical dimension for DICOM images (e.g. as created for various Radiology modalities). The following table shows the resultant DICOM objects:

| Pathology object | DICOM object |
| --- | --- |
| digital slide | DICOM study with four series |
| .25 micron/pixel image (80,000 × 40,000 pixels) | DICOM series #1 |
| 160 × 80 regions of size 500 × 500 pixels | 12,800 DICOM images in series #1 |
| 1 micron/pixel image (20,000 × 10,000 pixels) | DICOM series #2 |
| 40 × 20 regions of size 500 × 500 pixels | 800 DICOM images in series #2 |
| 4 micron/pixel image (5000 × 2,500 pixels) | DICOM series #3 |
| 10 × 5 regions of size 500 × 500 pixels | 50 DICOM images in series #3 |
| 16 micron/pixel image (1,250 × 750 pixels) | DICOM series #4 |
| 3 × 2 regions of size 500 × 500 pixels | 6 DICOM images in series #4 |

Note when images are not an even multiple of the region size, the DICOM module 110 truncates the regions at the right and/or bottom edge of the image. For example, on the 16 micron/pixel image the regions at the right edge are 250×500 pixels, the regions on the bottom edge are 500×250 pixels, and the region in the bottom right corner is 250×250 pixels. The DICOM standard allows images in a series to have varying dimensions.

The image viewer module 120 is configured to allow a user to view digital slide image data that is retrieved from a PACS system. The image viewer module 120 may be integral with the image capture device as shown or it may be located on a viewer station 40, or portions of the image viewer module may reside on one device (e.g., an image server) while other portions may reside on a separate device (e.g., a viewing station). The image viewing module 120 may comprise in part a viewing application, algorithm processing application, digital slide management system, or the like.

The TIFF file format typically used for storing digital slides in a single file enables specification of individual image dimensions and other information used to reassemble the image for later viewing or processing. Advantageously, the DICOM standard allows a similar function. In one embodiment, the DICOM module 110 is configured to store image attribute information (e.g., dimensions of regions, number of regions, resolution, magnification, etc.) in the header for each DICOM series, as a DICOM series corresponds to one resolution in a digital slide per the first table. Upon retrieval, this image attribute information from the header is used by the image viewer module 120 (e.g., at the image capture device 20, on the viewer station 40, or at an image server (not shown)) to facilitate reassembly of the digital slide image from the various DICOM images stored as the series. Similarly, the DICOM module 110 may also store digital slide attribute information in the header for a DICOM study. DICOM series and DICOM image attribute information are typically stored in various DICOM headers as provided in the current version of the specification.

Using this technique, a pathology digital slide or other large two-dimensional image may be stored in a PACS system and viewed from a PACS system as if it were a CT-Scan, MRI, or other radiology image. Each digital slide is a DICOM study, each DICOM study comprises a DICOM series corresponding to a resolution "level" of the digital slide, and each DICOM series comprises DICOM regions from the original image. A digital slide stored as a DICOM study may be associated with a DICOM case as any other study from another modality, and a DICOM case may comprise many studies from many different modalities. All study-oriented functions of the PACS system will work with these studies as they do for any other.

Each DICOM image may be retrieved and viewed separately but in order to view the pathology digital slide as a whole, the entire study must be retrieved and each DICOM series reassembled from its component DICOM images. For some applications it may not be necessary to access the pathology image at its highest resolution, in which case only the series corresponding to the required resolution level need be retrieved.

The image data in the stored DICOM images which comprise the regions of the digital slide may have varying color channels and depths. The data storage and retrieval technique is independent of the number and size of the color channels of each pixel. Typical pixel organizations include 12-bit or 16-bit grayscale, and 3×8=24-bit and 4×8=32-bit color.

The image data in the stored DICOM images which comprise the regions of the digital slide may be compressed. The techniques described herein are independent of the type and quality of the compression applied. Images may be stored with no compression ("raw"), or with lossless compression such as LZW (Lempel-Ziv-Welch), or with lossy compression such as JPEG or JPEG2000.

FIG. 3 is a flow diagram illustrating an example process for image capture and storage according to an embodiment of the present invention. Initially, in step 200 the microscope slide is scanned to create an image. Next, in step 210 the image is logically divided into regions, each of which are created as a DICOM image. Header information is included in the DICOM image header to orient the image data with respect to the other regions of the digital slide. All of the DICOM images that have the same resolution are then collected together and identified as a DICOM series, as shown in step 220. Then in step 230 a plurality of DICOM series are assembled to create a DICOM study, which is an equivalent structure to a digital slide. The DICOM study is then stored in the PACS or other data storage area as desired.

FIG. 4 is a flow diagram illustrating an example process for image retrieval and viewing according to an embodiment of the present invention. Initially, in step 300, a server receives a viewing request identifying a DICOM study or portion thereof that is desired for viewing. Next, in step 310 the corresponding DICOM image data is obtained from the PACS system. This may be done by obtaining the entire DICOM study or if the request identified a subset of the DICOM study, then the header information in the DICOM study, series, and images can be consulted to identify the appropriate data to return in response to the request. Once the image data have been returned, the alignment information in the header can be consulted to orient the image data relative to other image data, as seen in step 320 and then in step 330 the image data is displayed on the viewer station or other viewing apparatus or application to which the image data has been directed.

FIG. 5 is a block diagram illustrating a data mapping from a digital slide to a DICOM study according to an embodiment of the present invention. In the illustrated embodiment, the digital slide data structure is represented by the pyramid 450, which has multiple levels that each correspond to a different resolution. The baseline image 480 is the native resolution of the scanner while the intermediate levels and thumbnail level have reduced resolution.

In one embodiment, each level of a digital slide can be logically divided into separate regions, for example regions that are 500×500 pixels. Each of these regions can then be stored as a single DICOM image and collectively, all of the regions at the same resolution level in the digital slide pyramid (i.e., data structure) are identified in the PACS system as being in the same DICOM series. As shown in the illustrated embodiment, there are four resolution levels for this digital slide so there are also four DICOM series in the DICOM study that is stored in the PACS system. This correlation and the header information that is stored in the PACS system advantageously allow a digital slide to be reconstructed on a viewing platform after retrieval of imagery data from a PACS system.

Figure 6:
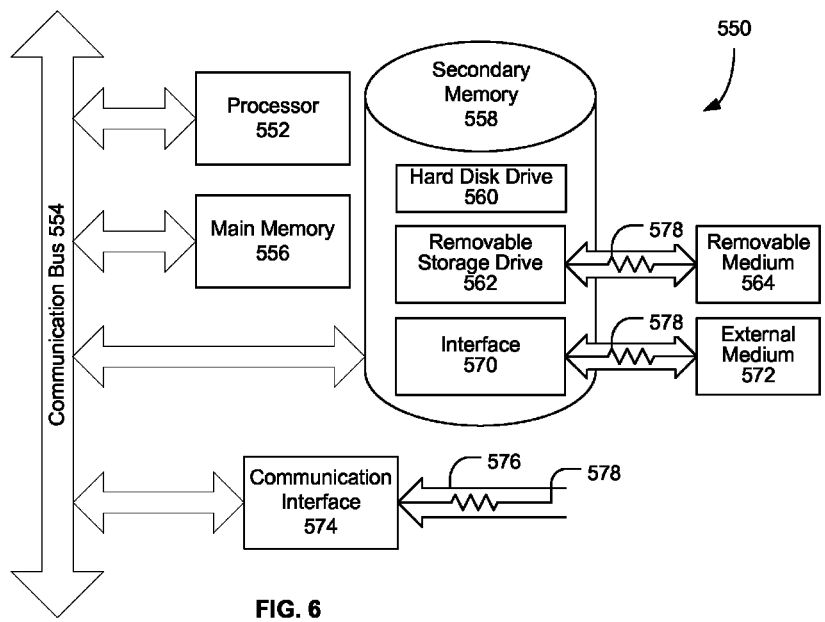
FIG. 6 is a block diagram illustrating an example computer system that may be used in connection with various embodiments described herein.

FIG. 6 is a block diagram illustrating an example computer system 550 that may be used in connection with various embodiments described herein. For example, the computer system 550 may be used in conjunction with an image capture device, PACS system, or viewer station as described with respect to FIG. 1. However, other computer systems and/or architectures may be used, as will be clear to those skilled in the art.

The computer system 550 preferably includes one or more processors, such as processor 552. Additional processors may be provided, such as an auxiliary processor to manage input/output, an auxiliary processor to perform floating point mathematical operations, a special-purpose microprocessor having an architecture suitable for fast execution of signal processing algorithms (e.g., digital signal processor), a slave processor subordinate to the main processing system (e.g., back-end processor), an additional microprocessor or controller for dual or multiple processor systems, or a coprocessor. Such auxiliary processors may be discrete processors or may be integrated with the processor 552.

The processor 552 is preferably connected to a communication bus 554. The communication bus 554 may include a data channel for facilitating information transfer between storage and other peripheral components of the computer system 550. The communication bus 554 further may provide a set of signals used for communication with the processor 552, including a data bus, address bus, and control bus (not shown). The communication bus 554 may comprise any standard or non-standard bus architecture such as, for example, bus architectures compliant with industry standard architecture ("ISA"), extended industry standard architecture ("EISA"), Micro Channel Architecture ("MCA"), peripheral component interconnect ("PCI") local bus, or standards promulgated by the Institute of Electrical and Electronics Engineers ("IEEE") including IEEE 488 general-purpose interface bus ("GPIB"), IEEE 696/S-100, and the like.

Computer system 550 preferably includes a main memory 556 and may also include a secondary memory 558. The main memory 556 provides storage of instructions and data for programs executing on the processor 552. The main memory 556 is typically semiconductor-based memory such as dynamic random access memory ("DRAM") and/or static random access memory ("SRAM"). Other semiconductor-based memory types include, for example, synchronous dynamic random access memory ("SDRAM"), Rambus dynamic random access memory ("RDRAM"), ferroelectric random access memory ("FRAM"), and the like, including read only memory ("ROM").

The secondary memory 558 may optionally include a hard disk drive 560 and/or a removable storage drive 562, for example a floppy disk drive, a magnetic tape drive, a compact disc ("CD") drive, a digital versatile disc ("DVD") drive, etc. The removable storage drive 562 reads from and/or writes to a removable storage medium 564 in a well-known manner. Removable storage medium 564 may be, for example, a floppy disk, magnetic tape, CD, DVD, etc.

The removable storage medium 564 is preferably a computer readable medium having stored thereon computer executable code (i.e., software) and/or data. The computer software or data stored on the removable storage medium 564 is read into the computer system 550 as electrical communication signals 578.

In alternative embodiments, secondary memory 558 may include other similar means for allowing computer programs or other data or instructions to be loaded into the computer system 550. Such means may include, for example, an external storage medium 572 and an interface 570. Examples of external storage medium 572 may include an external hard disk drive or an external optical drive, or and external magneto-optical drive.

Other examples of secondary memory 558 may include semiconductor-based memory such as programmable read-only memory ("PROM"), erasable programmable read-only memory ("EPROM"), electrically erasable read-only memory ("EEPROM"), or flash memory (block oriented memory similar to EEPROM). Also included are any other removable storage units 572 and interfaces 570, which allow software and data to be transferred from the removable storage unit 572 to the computer system 550.

Computer system 550 may also include a communication interface 574. The communication interface 574 allows software and data to be transferred between computer system 550 and external devices (e.g. printers), networks, or information sources. For example, computer software or executable code may be transferred to computer system 550 from a network server via communication interface 574. Examples of communication interface 574 include a modem, a network interface card ("NIC"), a communications port, a PCMCIA slot and card, an infrared interface, and an IEEE 1394 fire-wire, just to name a few.

Communication interface 574 preferably implements industry promulgated protocol standards, such as Ethernet IEEE 802 standards, Fiber Channel, digital subscriber line ("DSL"), asynchronous digital subscriber line ("ADSL"), frame relay, asynchronous transfer mode ("ATM"), integrated digital services network ("ISDN"), personal communications services ("PCS"), transmission control protocol/Internet protocol ("TCP/IP"), serial line Internet protocol/ point to point protocol ("SLIP/PPP"), and so on, but may also implement customized or non-standard interface protocols as well.

Software and data transferred via communication interface 574 are generally in the form of electrical communication signals 578. These signals 578 are preferably provided to communication interface 574 via a communication channel 576. Communication channel 576 carries signals 578 and can be implemented using a variety of wired or wireless communication means including wire or cable, fiber optics, conventional phone line, cellular phone link, wireless data communication link, radio frequency (RF) link, or infrared link, just to name a few.

Computer executable code (i.e., computer programs or software) is stored in the main memory 556 and/or the secondary memory 558. Computer programs can also be received via communication interface 574 and stored in the main memory 556 and/or the secondary memory 558. Such computer programs, when executed, enable the computer system 550 to perform the various functions of the present invention as previously described.

In this description, the term "computer readable medium" is used to refer to any media used to provide computer executable code (e.g., software and computer programs) to the computer system 550. Examples of these media include main memory 556, secondary memory 558 (including hard disk drive 560, removable storage medium 564, and external storage medium 572), and any peripheral device communicatively coupled with communication interface 574 (including a network information server or other network device). These computer readable mediums are means for providing executable code, programming instructions, and software to the computer system 550.

In an embodiment that is implemented using software, the software may be stored on a computer readable medium and loaded into computer system 550 by way of removable storage drive 562, interface 570, or communication interface 574. In such an embodiment, the software is loaded into the computer system 550 in the form of electrical communication signals 578. The software, when executed by the processor 552, preferably causes the processor 552 to perform the inventive features and functions previously described herein.

Various embodiments may also be implemented primarily in hardware using, for example, components such as application specific integrated circuits ("ASICs"), or field programmable gate arrays ("FPGAs"). Implementation of a hardware state machine capable of performing the functions described herein will also be apparent to those skilled in the relevant art. Various embodiments may also be implemented using a combination of both hardware and software.

Furthermore, those of skill in the art will appreciate that the various illustrative logical blocks, modules, circuits, and method steps described in connection with the above described figures and the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, circuit or step is for ease of description. Specific functions or steps can be moved from one module, block or circuit to another without departing from the invention.

Moreover, the various illustrative logical blocks, modules, and methods described in connection with the embodiments disclosed herein can be implemented or performed with a general purpose processor, a digital signal processor ("DSP"), an ASIC, FPGA or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such the processor can read information from, and write information to, the storage medium. In the alternative, the storage medium can be integral to the processor. The processor and the storage medium can also reside in an ASIC.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly limited by nothing other than the appended claims.

What is claimed is:

1. A non-transitory computer-readable medium having instructions stored thereon for storing a digital image using the Digital Imaging and Communication in Medicine (DICOM) standard, wherein the instructions, when executed by a processor, cause the processor to, for each of one or more digital images:
   divide the digital image at a first resolution into a first plurality of regions;
   store each of the first plurality of regions as a separate first DICOM images;
   associate each of the first DICOM images with a first DICOM series representing the digital image at the first resolution;
   obtain the digital image at a second resolution that is different than the first resolution;
   divide the digital image at the second resolution into a second plurality of regions;
   store each of the second plurality of regions as a separate second DICOM images;

associate each of the second DICOM images with a second DICOM series representing the digital image at the second resolution; and associate the first DICOM series and the second DICOM series with a DICOM study representing the digital image at a plurality of resolutions.

2. The non-transitory computer-readable medium of claim 1, wherein the one or more digital images comprises a plurality of digital images, and wherein the instructions further cause the processor to associate a first DICOM study, representing a first one of the plurality of digital images at a plurality of resolutions, and a second DICOM study, representing a second one of the plurality of digital images at a plurality of resolutions, with a DICOM case representing a plurality of digital images for a single patient.

3. The non-transitory computer-readable medium of claim 1, wherein the instructions further cause the processor to:
receive a request for the digital image at the first resolution; and,
in response to the request, retrieve one or more of the first DICOM images.

4. The non-transitory computer-readable medium of claim 1, wherein one or more of the first DICOM images have a different dimension than one or more other ones of the first DICOM image files.

5. The non-transitory computer-readable medium of claim 1, wherein the instructions further cause the processor to store alignment information for the first plurality of regions in one or more headers for one or more of the first DICOM images and the first DICOM series.

6. The non-transitory computer-readable medium of claim 5, wherein the instructions further cause the processor to:
receive a request for the digital image at the first resolution; and,
in response to the request, retrieve a plurality of the first DICOM images, and align at least a portion of the plurality of first DICOM images based on the alignment information.

7. A system for storing a digital image using the Digital Imaging and Communication in Medicine (DICOM) standard, the system comprising:
at least one hardware processor; and
one or more modules that, when executed by the at least one hardware processor, for each of one or more digital images,
divide the digital image at a first resolution into a first plurality of regions,
store each of the first plurality of regions as a separate first DICOM images,
associate each of the first DICOM images with a first DICOM series representing the digital image at the first resolution,
obtain the digital image at a second resolution that is different than the first resolution,
divide the digital image at the second resolution into a second plurality of regions,
store each of the second plurality of regions as a separate second DICOM images,
associate each of the second DICOM images with a second DICOM series representing the digital image at the second resolution, and
associate the first DICOM series and the second DICOM series with a DICOM study representing the digital image at a plurality of resolutions.

8. The system of claim 7, wherein the one or more digital images comprise a plurality of digital images, and wherein the one or more modules further associate a first DICOM study, representing a first one of the plurality of digital images at a plurality of resolutions, and a second DICOM study, representing a second one of the plurality of digital images at a plurality of resolutions, with a DICOM case representing a plurality of digital images for a single patient.

9. The system of claim 7, wherein the one or more modules further:
receive a request for the digital image at the first resolution; and,
in response to the request, retrieve one or more of the first DICOM image files.

10. The system of claim 7, wherein one or more of the first DICOM image files have a different dimension than one or more other ones of the first DICOM image files.

11. The system of claim 7, wherein the one or more modules further store alignment information for the first plurality of regions in one or more headers for one or more of the first DICOM images and the first DICOM series.

12. The system of claim 11, wherein the one or more modules further:
receive a request for the digital image at the first resolution; and,
in response to the request, retrieve a plurality of the first DICOM image files, and align at least a portion of the plurality of first DICOM image files based on the alignment information.

13. A method for storing a digital image using the Digital Imaging and Communication in Medicine (DICOM) standard, wherein the method comprises using at least one hardware processor to, for each of one or more digital images:
divide the digital image at a first resolution into a first plurality of regions;
store each of the first plurality of regions as a separate first DICOM images;
associate each of the first DICOM images with a first DICOM series representing the digital image at the first resolution;
obtain the digital image at a second resolution that is different than the first resolution;
divide the digital image at the second resolution into a second plurality of regions;
store each of the second plurality of regions as a separate second DICOM images;
associate each of the second DICOM images with a second DICOM series representing the digital image at the second resolution; and
associate the first DICOM series and the second DICOM series with a DICOM study representing the digital image at a plurality of resolutions.

14. The method of claim 13, wherein the one or more digital images comprise a plurality of digital images, and wherein the method further comprising using the at least one hardware processor to associate a first DICOM study, representing a first one of the plurality of digital images at a plurality of resolutions, and a second DICOM study, representing a second one of the plurality of digital images at a plurality of resolutions, with a DICOM case representing a plurality of digital images for a single patient.

15. The method of claim 13, further comprising using the at least one hardware processor to:
receive a request for the digital image at the first resolution; and,
in response to the request, retrieve one or more of the first DICOM image files.

16. The method of claim 13, wherein one or more of the first DICOM image files have a different dimension than one or more other ones of the first DICOM image files.

17. The method of claim 13, further comprising using the at least one hardware processor to store alignment information for the first plurality of regions in one or more headers for one or more of the first DICOM images and the first DICOM series.

* * * * *